United States Patent [19]

Fitzgerald, Edwin R.

[11] Patent Number: 5,081,870
[45] Date of Patent: Jan. 21, 1992

[54] METHOD AND APPARATUS FOR DETERMINING DYNAMIC MECHANICAL PROPERTIES OF MATERIALS

[76] Inventor: Fitzgerald, Edwin R., 2445 Tracey's Store Rd., Parkton, Md. 21120

[21] Appl. No.: 507,793

[22] Filed: Apr. 12, 1990

[51] Int. Cl.$^5$ .................. G01H 1/00; G01M 7/00; G01N 29/00
[52] U.S. Cl. .................................................. 73/575
[58] Field of Search .................. 73/575, 668, 576; 324/226, 234, 262

[56] References Cited

U.S. PATENT DOCUMENTS 2,774,239 12/1956 Fitzgerald.
3,830,099 8/1974 Ichihawa .............................. 73/668

OTHER PUBLICATIONS

Automated Measurement System for Dynamic Mechanical Properties of Viscoelastic Materials, Polymer Bulletin, 18, 1, 167–174 (1987), Edwin R. Fitzgerald and Roger E. Fitzgerald.
Method for Determining the Dynamic Mechanical Behavior of Gels and Solids at Audio Frequencies, J. Colloid Sci. 8, 1, 1–34 (1953) Fitzgerald, Ferry.
Temperature Magnitude Superposition of the Dynamic Mechanical Response of Tire Stocks, Polymer Bulletin, 8, 339–346, 1982, Fitzgerald and Ferry.
Audio-Frequency Mechanical Spectra of a Butadiene Terpolymer, J. Appl. Polymer Sci. 19, 2015–2031, 1975, Edwin R. Fitzgerald.
Viscoelastic Response of Intervertebral Disks at Audio-frequencies, Med. and Biol. Engr. 9, 459–478, 1970, Edwin Fitzgerald and Alan Freeland.
Dynamic Mechanical Properties of Stretched Natural Rubber, J. Accoust. Soc. Am. 33, 10, 1305–1314, 1961, Edwin Fitzgerald.
Yield Strength of Crystalline Solids from Dynamic Mechanical Measurements Developments in Mechanics, 1, pp. 10–38, 1961, Edwin Fitzgerald.
Dynamic Mechanical Measurements on Portland Cement Pastes During Setting and Curing, Materials Science and Engr. 7, 318–334, 1971, Edwin Fitzgerald.

Primary Examiner—Walter E. Snow
Attorney, Agent, or Firm—Larson & Taylor

[57] ABSTRACT

A method and apparatus is provided for dynamic mechanical measurements of materials in which a plurality of coplanar coils are disposed transversely with respect to a magnetic flux field. The coils are rigidly mounted to a plate and arranged so as to eliminate inductive coupling between the coils. Alternating current is passed through some of the coils so as to vibrate or oscillate the plate because of the alternating force resulting from the interaction of the electrical current and the magnetic field. Other of the coils have an alternating motional electromotive force (voltage) generated in them because of their vibration. The mechanical impedance of the plate is determined from the vector ratio of the vibration forcing current to the velocity sensing voltage. When the plate is connected to the material to be tested in vibration, measurements of the vector ratio of electrical current to motional voltage then provide determinations of dynamic mechanical properties at vibration frequencies from 0.1 to 100,000 Hz.

20 Claims, 8 Drawing Sheets

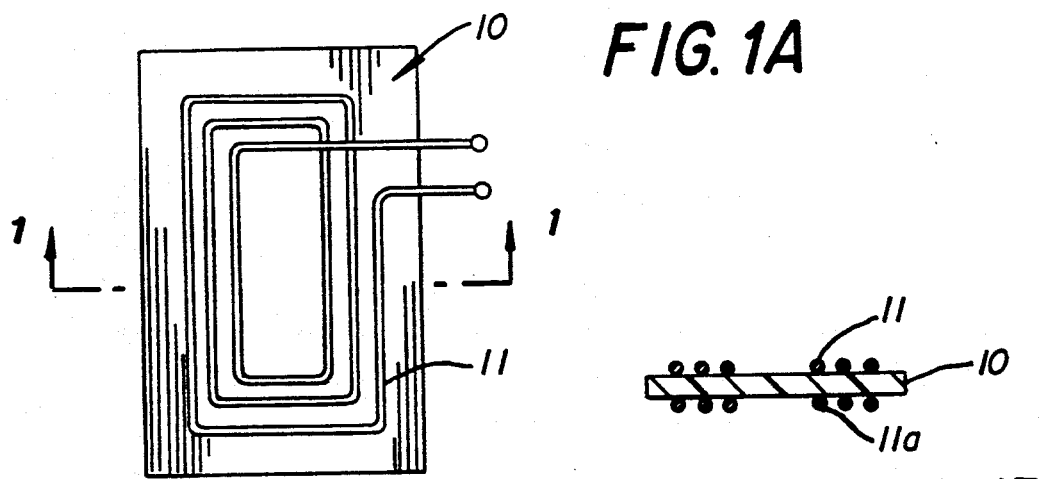
FIG. 1A
FIG. 1B
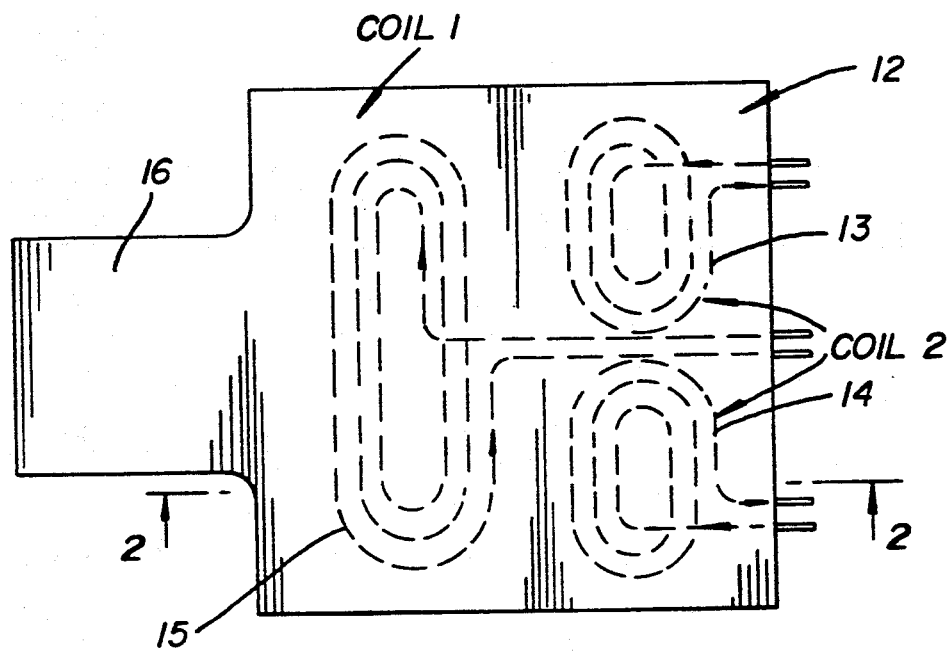
FIG. 2
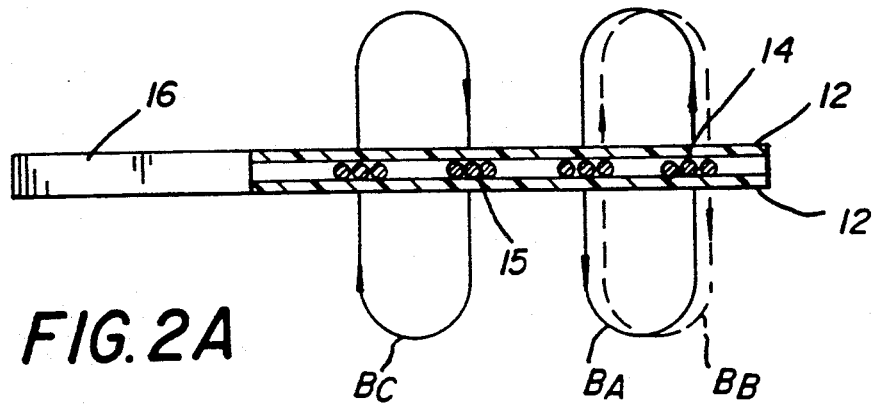
FIG. 2A

METHOD AND APPARATUS FOR DETERMINING DYNAMIC MECHANICAL PROPERTIES OF MATERIALS

FIELD OF THE INVENTION

The present invention relates to a method and apparatus for measuring the dynamic mechanical properties of various materials, including viscoelastic materials such as gels, plastics, and rubbers.

BACKGROUND OF THE INVENTION

In my prior U.S. Pat. No. 2,774,239 issued Dec. 18, 1956 there is disclosed an apparatus for determining the dynamic mechanical properties of viscoelastic materials. This previously patented apparatus and method has yielded the complex compliance and complex modulus of materials ranging from viscous liquids and soft gels, thermoplastics and elastomers, to hard solids such as quartz, lead, and stainless steel. Although this prior measurement method and apparatus have been successful, there are substantial and significant drawbacks and limitations. First the measurement requires two, separate alternating current electrical bridge balances. Further, the two coaxial coils used for excitation and for velocity sensing are tightly coupled electromagnetically through a soft iron pole piece, and a pre-balance must be made, before each bridge balance, in order to eliminate or minimize the (non-motional) mutual inductance voltage in the velocity sensing coil by means of auxiliary shielding and test coils. In addition, circular, coaxial coils are arranged to be in annular gaps between pole pieces whose reluctance decreases the magnetic flux density. Thus, a very large permanent magnet must be used to assure the necessary high value of magnetic flux density in the gap. This large magnet requirement and the iron pole pieces needed results in a large and massive apparatus which, in turn, prevents rapid temperature changes and slows the acquisition of information on temperature dependence of dynamic mechanical properties. Finally, the determination of the complex modulus at each frequency, because of the two necessary bridge balances and the prebalance to eliminate mutual inductance, requires 10 to 20 minutes.

The vibration excitation and sensing element in the prior apparatus consists of an aluminum alloy driving tube with coaxial coils as mentioned above, and it and the associated mechanical and electrical equipment are described in detail in U.S. Pat. No. 2,774,239.

SUMMARY OF THE INVENTION

The present invention overcomes the problems noted hereinbefore and provides a compact, efficient method and apparatus for rapidly obtaining accurate dynamic mechanical information on the material being tested. The invention employs a driving and sensing plate with flat, coplanar coils. The coils may be printed on the surfaces of the plate if it is a non-conductor, or printed on an insulating layer placed on the surfaces if the plate is metallic. Alternatively, the coils may be wound of fine wire and be cemented onto or embedded and cemented within the driving or sensing plate. The driving plate is disposed in a plane transverse to a magnetic flux field formed by pairs of magnets. A material to be tested is connected to the driving plate so that the test material is subject to stress and resulting deformation when current is passed through the coils in the plate.

It is known that the magnetic flux linkage or electromagnetic coupling between flat, coplanar coils is much less than that between two coaxial coils at the same separation distance, but when the flat coils are close together the induced EMF in one arising from alternating current in another will still be appreciable. This nonmotional, induced EMF can be reduced by arranging two coils in a non-coplanar configuration, i.e., with perpendicular planes, as described in Polymer Bulletin, Vol. 18, pp. 167-174 (1987). However, this non-coplanar coil configuration is inherently non-rigid at high vibration frequencies, requires a complicated magnetic field configuration, and as a practical matter, can not be easily adjusted to give zero inductive and capacitive coupling between the driving and sensing coils.

By contrast the coplanar, three-coil arrangement of the present invention is intrinsically extremely rigid. Two of the small coils are provided to have identical dimensions and the same number of turns, but have reversed winding directions. Thus, the induced EMFs in each of these two sensing coils from the current in the third, driving Coil are exactly 180° out of phase, and cancel. However, since the directions of the magnetic fields between pairs of permanent magnets are also reversed for each of the two sensing coils, then the motional EMFs in each of these coils will add. Thus, the present invention provides a means to eliminate the inductive coupling between the coils in the driving plate. Further, the structural arrangement provided by the present invention eliminates the need for two separate alternating current bridge balances and the need for a very large permanent magnet as was essential in the prior art device described hereinbefore.

An object of the present invention is to provide a small, compact apparatus for rapidly producing dynamic mechanical measurements of various materials.

Another object of the present invention is in providing a plurality of coplanar coils rigidly mounted on a plate disposed transversely in a magnetic flux field and so arranged as to eliminate inductive coupling between the coils.

Other objects and many of the attendant advantages of the present invention will become more apparent when considered in connection with the accompanying drawings

BRIEF DESCRIPTION OF THE DRAWINGS

FIG. 1A is a plan view of a flat, spiral coil of rectangular shape, cemented to a rigid plate, FIG. 1B is a cross section of the coil and plate of FIG. 1A along the lines 1—1 of FIG. 1A, FIG. 2 is a plan view of a typical drive plate with coils disposed within the drive plate, FIG. 2A is a cross sectional view of the drive plate along the lines 2—2 of FIG. 2, wherein the transverse magnetic field directions are indicated.

DETAILED DESCRIPTION OF THE PREFERRED EMBODIMENTS

Figure 3:
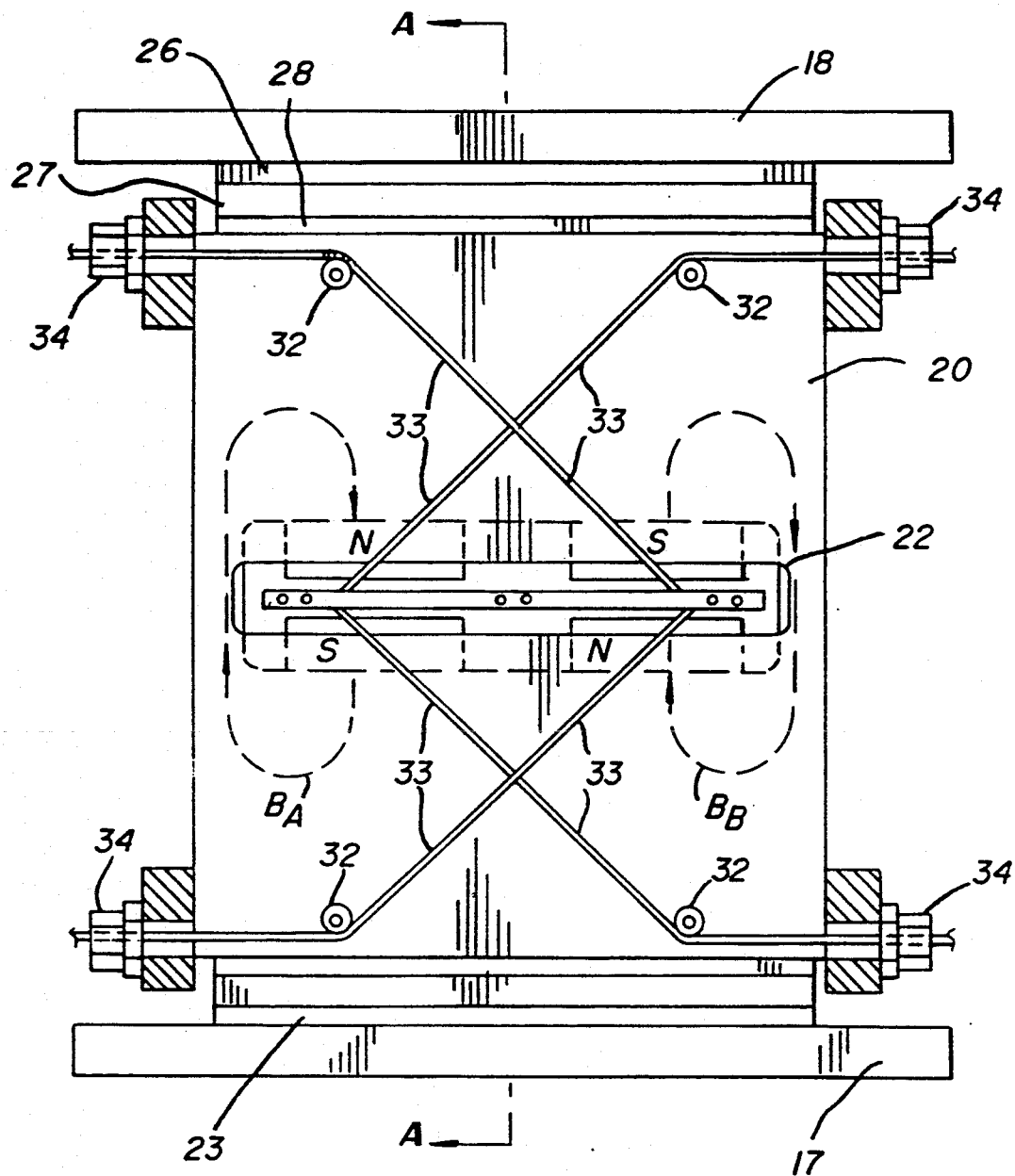
FIG. 3 is an elevational back view of the assembled electromagnetic shear transducer.

The method and apparatus described herein may be used for determining the dynamic mechanical properties of solid, gel, and liquid materials including, but not limited to, plastic and rubber-like solids which are commonly called viscoelastic. Measurements on aluminum, steel, and other metals, and on crystals such as quartz, rock salt, and others can be made with this apparatus. It is also possible to use the present invention for measurements of dynamic mechanical properties of bone, intervertebral disks, and other animal tissues. Measurements on bio-polymers thus are possible and can be related to the physiological functions and state of the bio-material measured.

A determination of the dynamic mechanical properties of materials is an important prerequisite to the design of structures and devices which will be subject to vibration, and also is necessary in efforts to control noise and/or vibration of machinery, automobiles, airplanes, and trucks. Dynamic mechanical measurements provide the basic information needed in attempts to reduce the energy loss from the heating of rolling tires and in calculations of power loss in tires. A reduction in the tire power loss will substantially increase the travelled miles per gallon of fuel burned.

The present invention provides a means to measure the dynamic mechanical properties of materials and to measure these properties over a continuous and wide range of vibration frequencies and of temperature. Measurements of dynamic mechanical properties while a material is simultaneously under steady tensile or compressive mechanical loading can be made. The apparatus and method disclosed herein measure dynamic mechanical properties while a material is simultaneously subject to a D.C. or A.C. electrical field, and/or allows for simultaneous measurement of dynamic electrical properties while the material is undergoing mechanical vibrations and/or steady mechanical loading. The invention provides improved, simple, accurate, and precise means for these measurements. The invention provides measurements of complex viscosity, complex fluidity, complex shear modulus and shear compliance and related quantities, such as shear sound velocity and attenuation, as well as complex tensile and compressive modulus and compliance, and related quantities. The materials on which such measurements may be made range from liquids and soft gels to hard or stiff solids over continuous temperature and frequency ranges from −100° to 150° C. and 0.1 to 100,000 cycles per second.

Referring more specifically to the drawings wherein like numerals disclose like parts throughout several views there is shown in FIG. 1A a plan view of a plate 10 having a flat, spiral, rectangular coil 11 mounted thereon. The plate 10 may may be made of a hard, rigid nonconductive material and the coil may be of fine copper or aluminum wire (e.g., 0.002 to 0.005 inch diameter) with insulated coating. The coils utilized in the present invention, may have from 500 to 1000 turns. The coil 11 may be of fine wire cemented to the support plate 10 with a rigid adhesive such as epoxy cement or alternatively the coil may be printed on the plate. FIG. 1B shows schematically a coil 11 mounted on one side of plate 10 and a further coil 11A mounted on the opposite side of plate 10.

In the event the coils 11 and 11A are printed on the plate, the plate 10 may be a nonconductor or metallic with an insulating layer thereon. An anodized surface on an aluminum plate may serve as an insulating layer or a high resistance silicon wafer may have coils printed directly thereon. A plate formed of a semiconductor may be doped to provide internal conducting paths in the patterns of flat, rectangular coils.

Figure 3A:
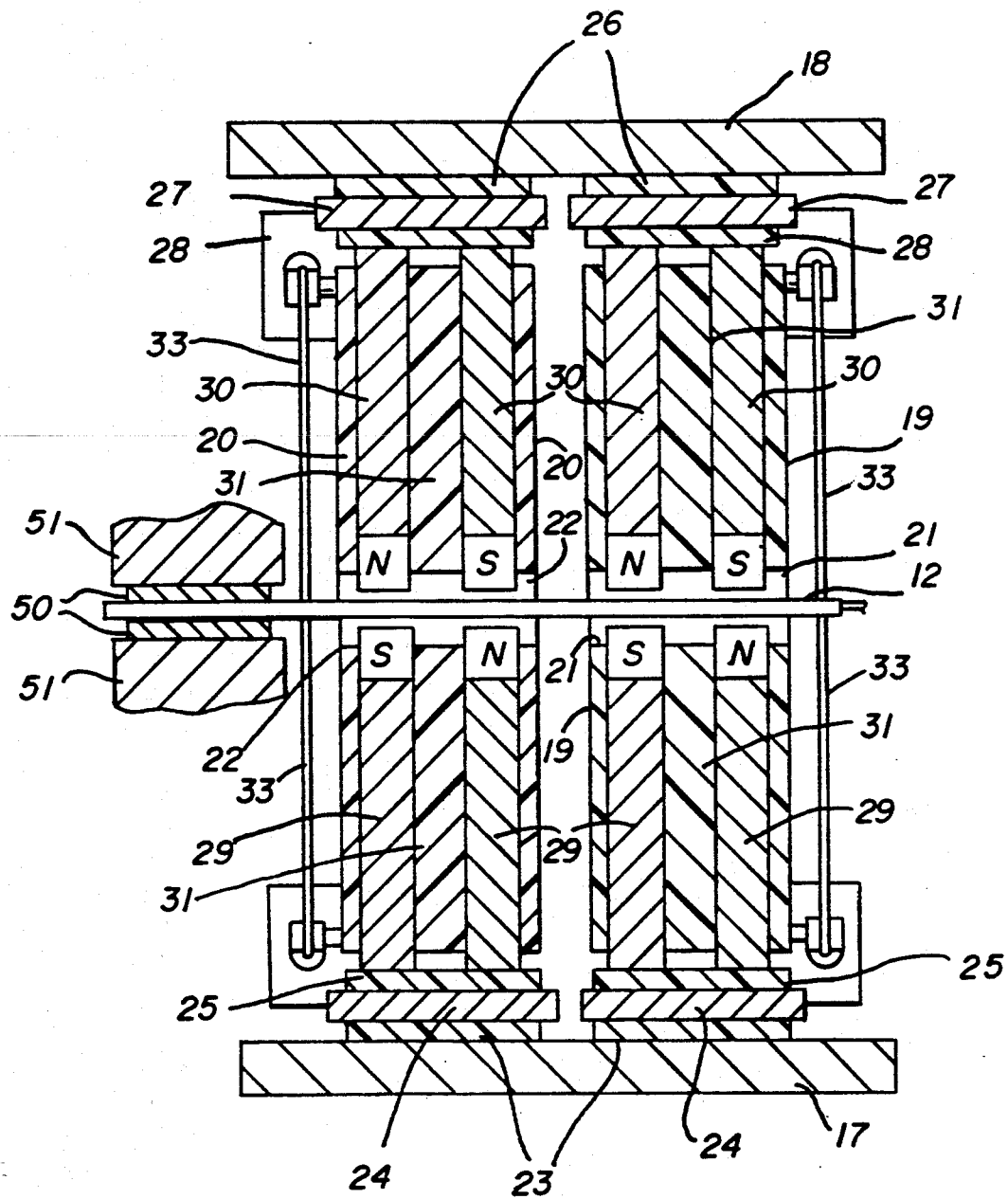
FIG. 3A is a cross sectional view of the electromagnetic shear transducer along the lines A—A of FIG. 3, and shows an arrangement for the measurement of shear compliance or modulus.

FIG. 2 discloses schematically a drive plate 12 having a pair of velocity sensing coils 13 and 14 disposed between the outer surfaces of plate 12 as shown in FIG. 2A. The sensing coils 13 and 14 which are connected in series have identical dimensions and the same number of turns, from 500 to 1000 turns, but have reversed winding directions. The larger, centrally located driving coil is shown at 15. The directions of the transverse magnetic fields across coils 15, 13, 14 are denoted in FIG. 2A by $B_C$, $B_A$, and $B_B$ respectively. The drive plate 12 has a reduced end portion 16. FIGS. 3 and 3A disclose in elevation and in cross section the assembled electromagnetic shear transducer having a base plate 17 and top plate 18. The base and top plates are made of a hard, rigid nonmagnetic material such as laminated phenolic, aluminum alloys or stainless steel. There are further provided pairs of end plates 19 and 20 disposed at each end of a set of magnets and these are provided with central slots 21 and 22 respectively to receive the drive plate 12.

The baseplate 17 has secured thereto a pair of blocks 23 of vibration isolation and insulating material which may be made of rubberized cork gasket material, silicone rubber or laminations of cork and rubber. In addition there may be plates of nonmetallic material or metal surrounded by rubber or cork gasket material. Fixed to the upper surfaces of the blocks 23 are slightly larger blocks 24 which are formed of hard rigid nonmagnetic material similar to the material of the baseplate 17. Secured to the upper surfaces of the blocks 24 are blocks 25 which are identical to blocks 23. The combination of the base plate 17 together with the blocks 23, 24 and 25 provide a vibration isolation and insulating supporting structure for the magnets and holders. There is an identical supporting structure affixed to the top plate 18 in the form of blocks 26, 27 and 28 corresponding respectively to blocks 24, 25 and 26.

Secured to the blocks 25 and 28 are magnet holders' bottoms 29 and tops 30 respectively. The magnet holders are made of solid or laminated soft iron or mild steel with high magnetic permeability and low magnetic reluctance. The magnets, of high strength, rare earth composition, are affixed to the inner surfaces of slots in the magnet holders and have the polarity as shown in FIGS. 3 and 3A. There are provided magnet holder spacers 31 which are disposed between the magnet holders 29, 30. The spacers are made of hard, rigid nonmagnetic material such as aluminum, stainless steel or plastic. The magnet sets including the end plates, magnet holders, magnets and spacers are held together by means of machine screws not shown in FIG. 3, 3A. There may also be provided a housing (not shown) of cover plates to enclose the sides and back.

The drive plate 12 is suspended within the air gap between the magnets and within the slots 21 and 22 in end plates 19 and 20 respectively. Fine, non-magnetic (e.g., stainless steel or phosphor bronze) wires 33 are attached to the driving plate 12 and affixed to adjusting screws 34 have grooved heads in which the support wires 33 are fitted and turned into the adjusting machine screws 34. The wires 33 permit longitudinal movement of the driving plate 12 in a plane transverse to the field of magnetic flux within the air gap but prevent movement of the driving plate in other directions.

As shown in FIG. 3A, for dynamic mechanical measurements in shear a pair of samples 50, in the form of plates or disks, are pressed against the portion of the driving plate extending beyond the support wires 33 by sample clamps 51 which are fixed against motion in the direction of vibration.

Figure 4:
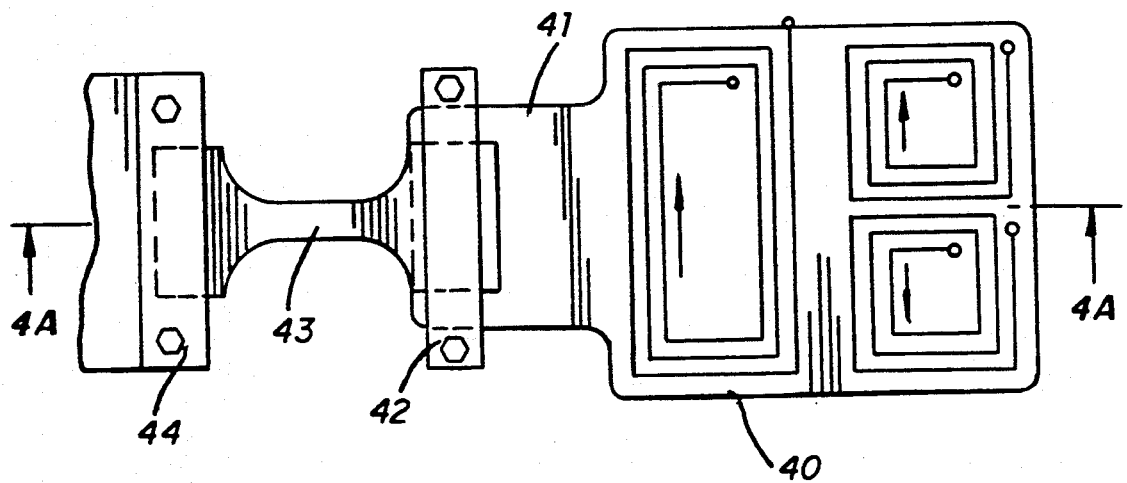
FIG. 4 is a diagrammatic plan view of an arrangement for measurement of extensional compliance or modulus.
Figure 4A:
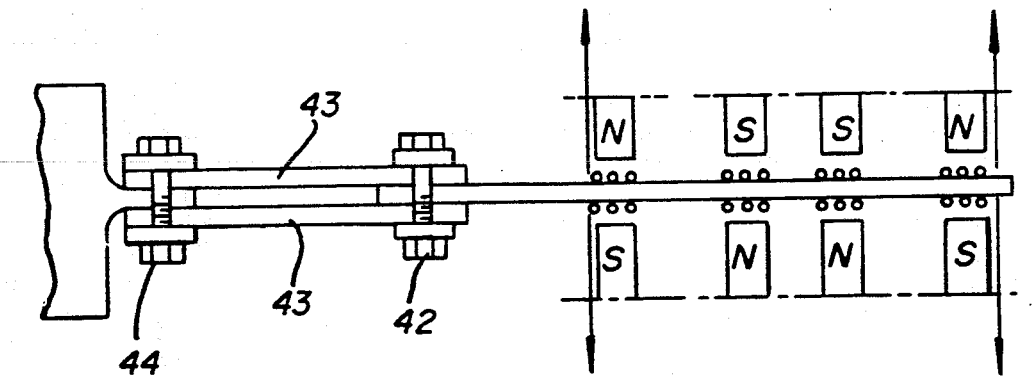
FIG. 4A is a sectional view along the lines B—B of FIG. 4.

When dynamic measurements of a sample material in extension are to be made a driving plate 40 as shown in FIG. 4 has the reduced end portion 41 provided with a clamp 42 to retain end portions of a pair of sample materials 43. The opposite ends of the samples are held by a clamp 44 and secured to a fixed support. When the driving coils in the plate are energized the magnetic flux within the air gap causes the plate to vibrate or oscillate. By means of the voltage produced in the sensing coil by the vibration the extensional compliance or modulus of the sample material can be determined from the complex/vector ratio of the driving coil current to the sensing coil voltage as described hereinafter.

Figure 5:
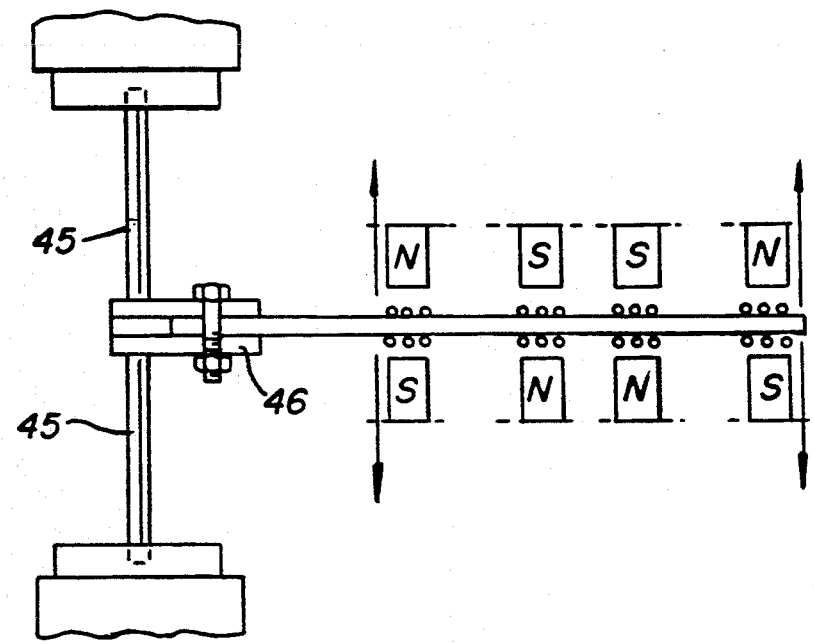
FIG. 5 is a diagrammatic side elevation showing an arrangement for determining the flexural properties of a strip of material, FIG. 6 discloses in plan view an arrangement for measuring extension properties of a stiff, hard material.

In FIG. 5 there is shown sample material 45 which is retained between clamp 46 attached to a driving plate 50 and a fixed structure at the opposite end. With this arrangement the flexural compliance or modulus of the sample material can be measured.

Figure 6:
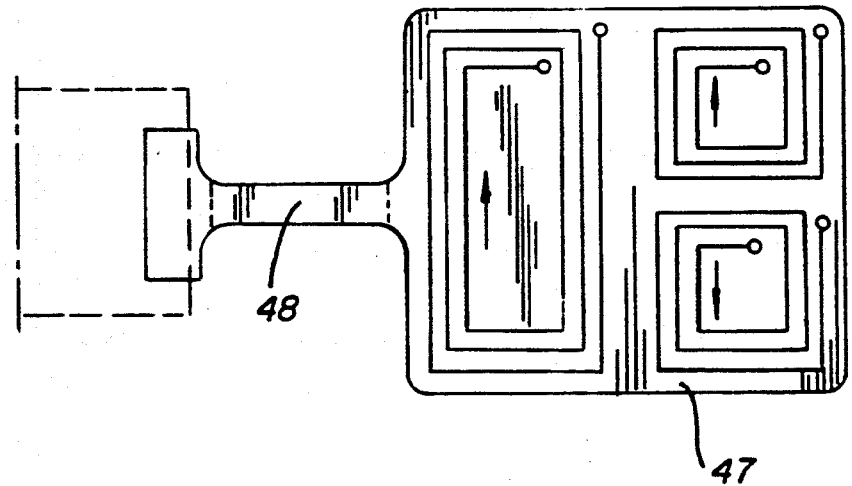

In FIG. 6 there is shown a driving plate 47 which is made of sample material and has a reduced end portion 48 of sample material. The outer end of portion 48 is retained by a clamp so that the extensional compliance or modulus of the sample material may be determined.

Figure 9A:
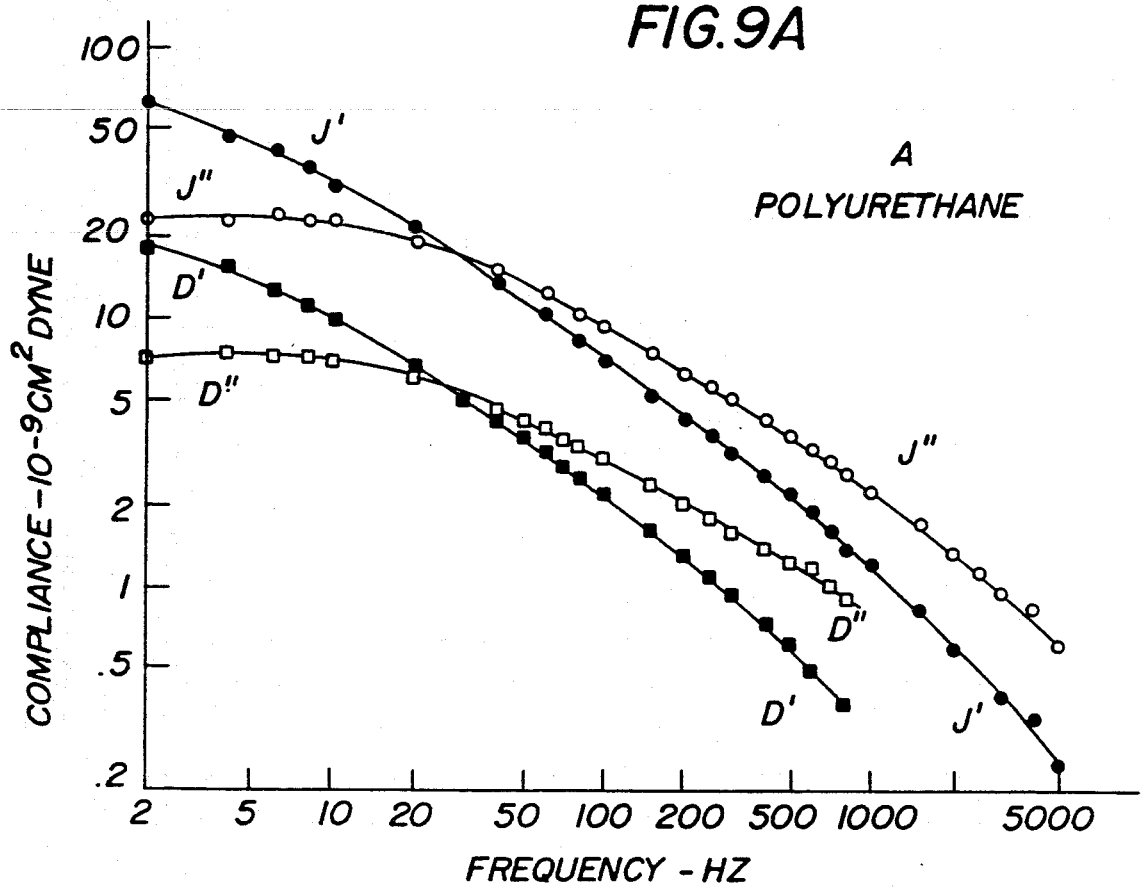
FIG. 9A shows curves of complex shear and complex extensional compliance obtained from the automated measurement system for a polyurethane rubber.
Figure 9B:
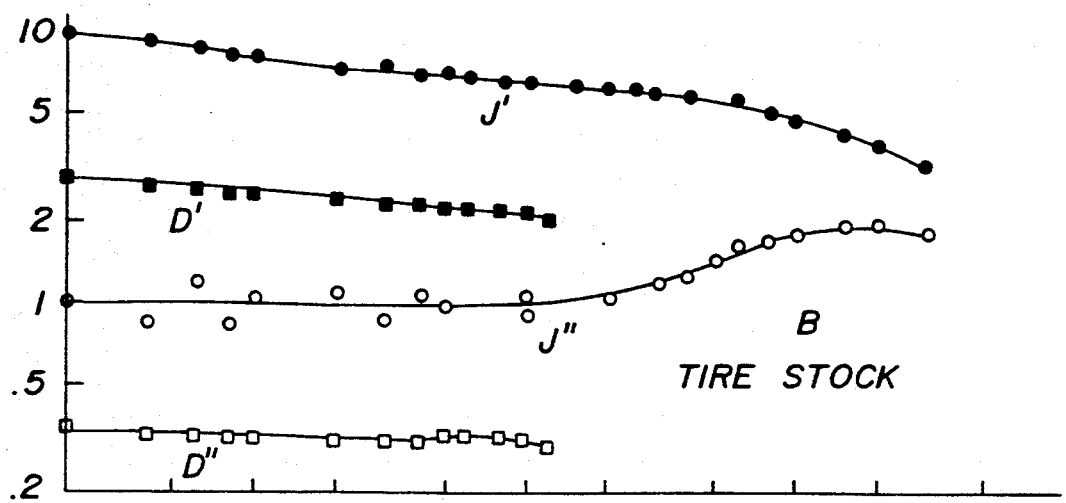
FIG. 9B shows curves of complex shear and extensional compliance obtained from the automated measurement system for a tire tread stock rubber.

FIGS. 9A and 9B illustrate curves of complex shear and extensional compliance obtained from the automated flexure measurement systems, according to the present invention, for a polyurethane rubber and a tire tread stock rubber.

Figure 10:
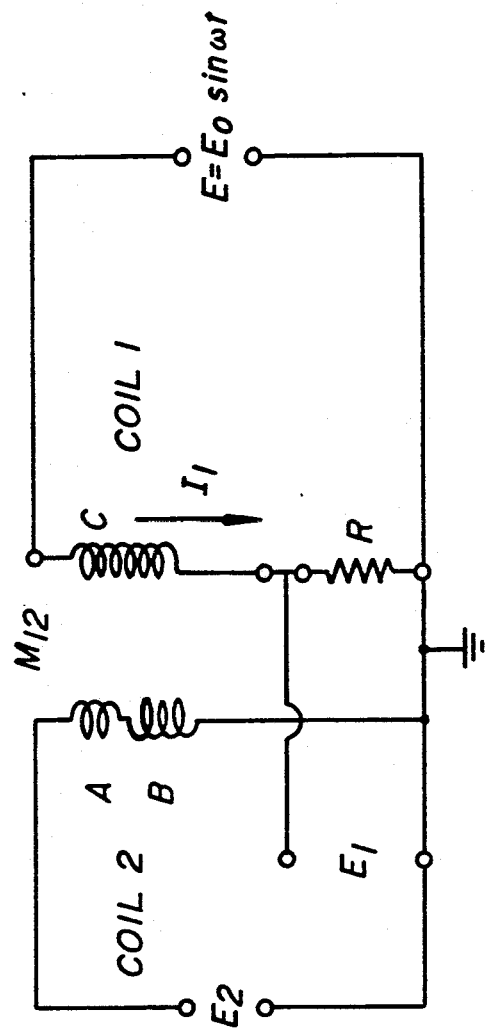
FIG. 10 shows the electrical circuit arrangement for measurement of the complex ratio of the current in the force coil, 1 to the motional electromotive force in the velocity sensing coil, 2, with parts, A, B.
Figure 8:
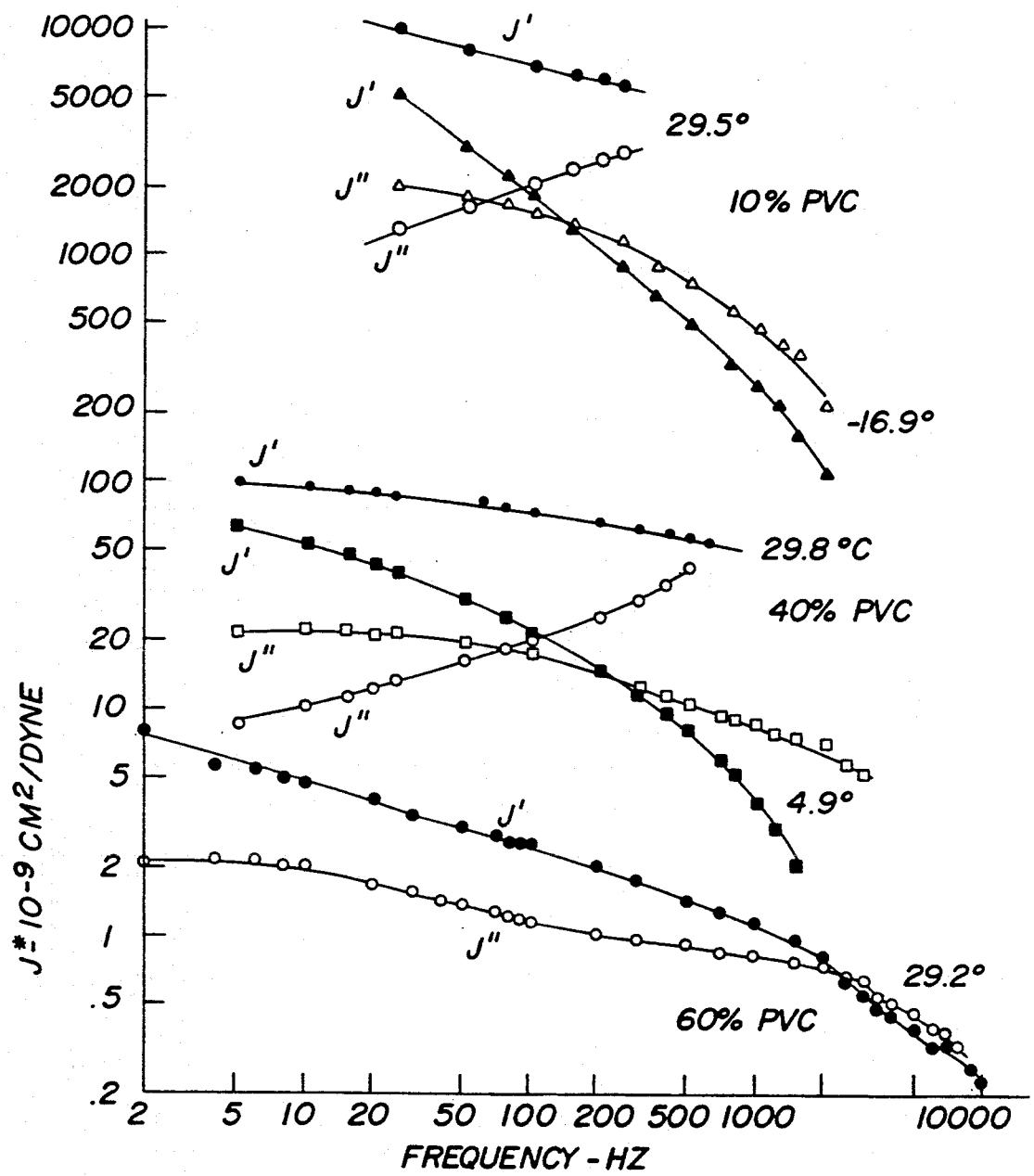
FIG. 8 shows curves which demonstrate the frequency variation of complex shear compliance obtained from the automated measurement system of FIG. 7 for compositions of polyvinyl chloride (PVC) and di-octyl phthalate ranging from a soft gel (10% PVC) to a flexible rubber, (40% PVC) and to a stiff material (60% PVC)

FIG. 10 discloses the circuit for measurement of the ratio of the current in the force coil 15 to the motional electromotive force in the velocity sensing coils A and B corresponding to the coils 13 and 14 shown in FIG. 2. Coils A and B are oppositely wound so as to eliminate the mutual inductance between the coils. The coil corresponds to the coil 15 of FIG. 2. Coils A and B are the velocity sensing coils and coil is the current, driving coil although, if desired, the functions of the coils may be interchanged. Mutual inductance, $M_{12}$, between coils A and B and coil is eliminated so that $E_2$ represents only the motional EMF across the coils A and B and $E_1$ the voltage across R which is $I_1R$ where $I_1$ is the current through coil and the resistance, R.

The relevant physical properties of a material subject to vibration consist of a complex compliance or a complex modulus defined as the (vector) ratio of alternating strain to stress or alternating stress to strain, respectively. Thus for vibration in shear with an applied alternating, sinusoidal stress of frequency, f, $$s(t) = s_o \sin 2\pi f t \tag{1}$$

the resulting strain will be partly in phase and partly 90° out of phase with the stress because of the elastoviscous (viscoelastic) nature of all real materials.

$$a(t) = a'_o \sin 2\pi f t - a''_o \cos 2\pi f t \tag{2}$$

and this yields the definition of a complex shear compliance $$J^* = J' - iJ'' \tag{3}$$

where $J' = a'_o/S_0$; $J'' = a''_o/S_0$. A complex shear modulus can also be used to describe the material response to a time-dependent stress where $$G^* = 1/J^* = G' + iG'' \tag{4}$$

Materials vibrated in extension or compression can similarly be characterized by a complex extensional compliance, $D^* = D' - iD''$, or a complex extensional modulus, $E^* = E' + iE''$. Flexural or torsional vibrations can likewise be related to relevant complex moduli and compliances. In every case a proper characterization or evaluation of the vibration response of a material requires a knowledge of its dynamic mechanical behavior, as described by these moduli or compliances, over a range of temperatures, vibration frequencies, and as modified by steady loads, loading history, microstructures, together with other ambient conditions.

Excitation/vibration of the driving plate is caused by an alternating current, $I_1 = I_0 \sin \omega t$, through the current (driving) coil 15 (FIGS. 2, 2A) while it is suspended between the opposite poles of the permanent magnets as shown in FIGS. 3 and 3A. Since the coil "wires" (or printed conducting paths) are perpendicular to the magnetic field, the driving force according to Ampere's law is, $$F_1 = B_1 l_1 I_0 \sin \omega t \tag{5}$$

where $B_1$ ($B_C$, FIGS. 2A, 3) is the perpendicular magnetic flux density in the air gap between magnets, $l_1$ is the length of the driving coil turns that are in the magnetic field, and $\omega = 2\pi f$, where f is the frequency of oscillation (vibration).

As a result of this alternating force the plate will oscillate with the same frequency, but out of phase, with velocity, $$v = v_0 \sin(\omega t - \delta) \tag{6}$$

and such that an alternating, open circuit, motional EMF, $E_2$ will be generated in the velocity (sensing) coils 13, 14 (FIGS. 2, 2A) which are connected in series, according to Faraday's law, $$E_2 = B_2 l_2 v_0 \sin(\omega - \delta) \tag{7}$$

where $B_2$ ($B_A$, $B_B$, FIGS. 2A, 3) is the (perpendicular) magnetic flux density in the gap at the location of the velocity coil, $l_2$, is the length of velocity coil 13, 14 turns that are in the magnetic field, and $\delta$ is the phase shift between the driving current and the velocity.

The mechanical impedance ($Z_{Mp}$) of the suspended driving plate by definition is the vector ratio of force/velocity so that, $$Z_M = Z_{Mp} = B_1 l_1 B_2 l_2 \frac{I_1}{E_2} \tag{8}$$

$$= K^2 \frac{I_1}{E_2} \tag{8a}$$

where $I_1$, $E_2$, are the rms vector values of driving current and motional EMF, and $K^2 = B_1 l_1 B_2 l_2$. The suspended driving plate mechanical impedance will result from air resistance, $R_a$, elastance of the suspension wires, $S_w$, and the inertial mass, $M_p$, of the driving plate.

$$Z_{Mp} = R_a + i\left(\omega M_p - \frac{S_w}{\omega}\right) \tag{9}$$

When samples (50 FIG. 3A) of impedance, $Z_{Ms}$, are clamped 51 against the driving plate 12, the measured mechanical impedance is increased to, $$Z_M' = Z_{Mp} + Z_{Ms} \tag{10}$$

and the measured vector ratio of driving current to motional EMF will change to $I_1'/E_1'$. Thus, in this system, it is only necessary to find the vector (or complex) ratio of current to voltage with and without a sample at each frequency of measurement to obtain the sample impedance, $Z_{Ms}$.

$$Z_{MS} = K^2 \left(\frac{I_1'}{E_2'} - \frac{I_1}{E_2}\right) \tag{11}$$

Once the mechanical impedance of the sample pair is known, the complex compliance or modulus can be calculated from the sample dimensions. For shear vibration of two disk-shaped samples, for example, $$J^* = J' - iJ'' = \frac{-i}{2\pi f} \frac{A}{h} Y_{Ms}^* \tag{12}$$

where A is the cross sectional area of both samples, h is the thickness of each, $i = \sqrt{-1}$, and $Y_{Ms}^* = 1/Z_{Ms}^*$ is the sample complex (vector) mechanical admittance.

In order to get reliable results at high frequencies, it is necessary that the driving plate inertial mass be small so that the sample impedance is comparable to the driving plate impedance. If not, the driving plate impedance ($\sim 2\pi f M_p$) becomes so large compared to the sample impedance that the difference between the current-/voltage ratios with and without samples is very small and the results become unreliable.

If the magnetic flux density is high, the "sensitivity constant", $K^2$, can be large for small coils and small plates which yield low values of inertial mass. Therefore, the flat coil configuration used in this invention has the added advantage that no reduction in magnetic flux density results from the use of pole pieces or cores; the magnetic flux density is produced directly between permanent magnet poles. For best results, the ratio $K^2/m$ should be high; an increase of $K^2/m$ ratio from 10 to 100 times that of the apparatus described in U.S. Pat. No. 2,774,239 is possible in the present invention.

In order to find both the magnitude and phase (and thus the in-phase and 90° out of phase components) of the $I_1/E_2$ and $I_1'/E_1'$ current to voltage ratios, a vector electrical impedance or admittance measurement method is needed, but there are many of these available. An electrical oscillator with quadrature outputs (exactly 90° out of phase) allows separate null balancing of the in-phase and 90° out-of-phase components of the motional EMF relative to the driving current, for example.

The velocity coils can alternatively be placed in one arm of the electrical impedance bridge circuit described in U.S. Pat. No. 2,774,239 and its dynamic electrical impedance determined for two known vector ratios of electrical current, $I_1/I_2$, in the driving (current) coil and in the driven (velocity) coils, respectively, as described in that patent.

Other electrical circuits and devices, phase meters, vector impedance meters, frequency response analyzers, etc. can be used to find the necessary current to voltage ratios.

This invention provides a means for an absolute calibration of the electromagnetic transducer constant, $K^2$, when values of the mechanical impedance of the suspended driving plate, $Z_{Mp}$, are measured as a function of the frequency of vibration, f. That is, the 90° phase component of driving plate mechanical impedance is (Eq. 9), $$X_{Mp} = \omega M_p - \frac{S_w}{\omega} \tag{13}$$

and therefore, $$\omega X_{Mp} = -S_w + M_p \omega^2 \tag{13a}$$

At each frequency the current ratio $I_1/E_2 = Y_{12}^*$ will have an in-phase and 90°-phase component $$I_1/E_2 = Y_{12}^* = G_{12} + iB_{12} \tag{14}$$

which, when multiplied by $K^2$ are equal to the in-phase and 90°-phase components of driving plate mechanical impedance. Therefore, $K^2 B_{12} = X_{Mp}$, and $$\omega B_{12} = \frac{-S_w}{K^2} + \frac{M_p \omega^2}{K^2} \tag{15}$$

From Eq. 15 above, it can be seen that if $M_p$ is known, the value of $K^2$ can be found by plotting $\omega B_{12}$ vs. $\omega^2$ to yield a straight line of intercept $-S_w/K^2$ and slope $M_p/K^2$. From the known mass of the driving plate, $M_p$, and the measured slope, the constant, $K^2$ can be calculated as can the support wire elastance, $S_w$.

With either the driving plate or the sample holder insulated above electrical ground (cf. FIGS. 2,3) a direct or alternating current electrical field can be applied between the sample holders and the driving plate during mechanical impedance measurements to ascertain possible effects of such electrical fields on the dynamic mechanical properties of materials. It is also possible to measure the complex dielectric constant and/or AC or DC resistivity of insulating materials while they are being vibrated in shear in this apparatus.

It is obvious that by equal compression of the samples between the sample holders and the plate, the effects of compressive stress perpendicular to the vibration direction on dynamic mechanical properties can be found.

Strips of sample materials can also be stretched transversely or in line with the vibration direction during dynamic mechanical measurements to study the effects of extensional stresses and/or elongations on dynamic mechanical properties and/or on dielectric properties.

A simple variation of this invention to allow for measurement of extensional modulus or compliance is shown in FIG. 4. It is obvious that bars or strips of material fixed transversely to the driving plate vibration direction will allow for measurements of the flexural vibration properties of such bars or strips as indicated in FIG. 5.

It is necessary to suspend the driving plate in the magnetic gaps of the permanent magnets by means of long, thin wires which keep it centered and fixed, but allow vibration in its longitudinal direction in order to measure liquids and soft gels. However, in measuring stiff, solid samples it is possible to hold the driving plate and coils in the magnetic fields of the permanent magnets by shear samples of equal thickness between the sample holders and the driving plate, for example.

For stiff, solid samples such as metals and metal alloys, it is also possible to print coils, over an insulating layer, directly on a part of the material to be tested as shown in FIG. 6. In this case, the sample and driving plate are integral parts of the same piece, but the sample test section, of smaller cross section, will deform when vibrated with one end fixed while the parts of the driving plate where the coils are located will not deform. This scheme is particularly useful for determining the dynamic mechanical extensional modulus or compliance as illustrated in FIG. 6. The electromagnetic transducer constant, $K^2$, and the support wire and driving tube mechanical impedance, $Z_{Mp}$, are determined for each sample in this case before one end of the test section is clamped to give the additional sample mechanical impedance, $Z_{Ms}$. If the stiff, solid material is a nonconductor, the current coil and velocity coil can be printed directly on the sample.

The sample holder and/or clamping device can be rigidly mounted to the apparatus frame or housing as shown schematically in FIGS. 3 and 4, but in order to avoid possible coupling to vibrational modes of the entire apparatus, the sample clamps can alternatively be housed in a compact, massive structure which is isolated from the apparatus frame; because of its great mass, such a sample holder device will not vibrate except at the lowest frequencies where its vibration can be measured and taken into account in determining the sample mechanical impedance.

In the preceding description of this invention, the single large coil shown in FIG. 2 was used as the driving coil, 15, in which an alternating electrical current was put in order to produce the vibrating force. The two small coils (13 and 14) in series but with reversed winding directions comprised the velocity-sensing coils needed to determine the mechanical impedance/admittance. However, it is clear that the coil functions can be interchanged; that is, alternating electrical current passed through the two small coils will produce a vibrating force while the single large coil can become the velocity sensing coil. In either case, the net inductive coupling between the three coils will be eliminated as needed for this measurement method. Further, to obtain exactly zero inductive coupling, the amount and phase of the current in each of the two small coils can be adjusted if necessary when they are used to produce the driving force. Conversely, when used as velocity sensing coils, the electromotive force (EMF) from each of the two small coils can be adjusted to bring their net induced, non-motional EMFs exactly equal to zero.

It is also an important feature of this invention that vibration reduction/isolation means/materials are used to prevent the vibrating force produced by the driving coil or coils from causing any vibration of the permanent magnet holders or magnets producing the magnetic fields across the velocity sensing coil or coils; such vibrations cause corresponding vibratory motion of the magnetic fields and a spurious EMF in the sensing coil.

A thin metal shield insulated from but extending across both sides of the vibrating force coil prevents capacitive coupling with the velocity sensing coil.

From the measured values of complex modulus, it is also possible to calculate the relevant sound velocity and attenuation of materials.

Figure 7:
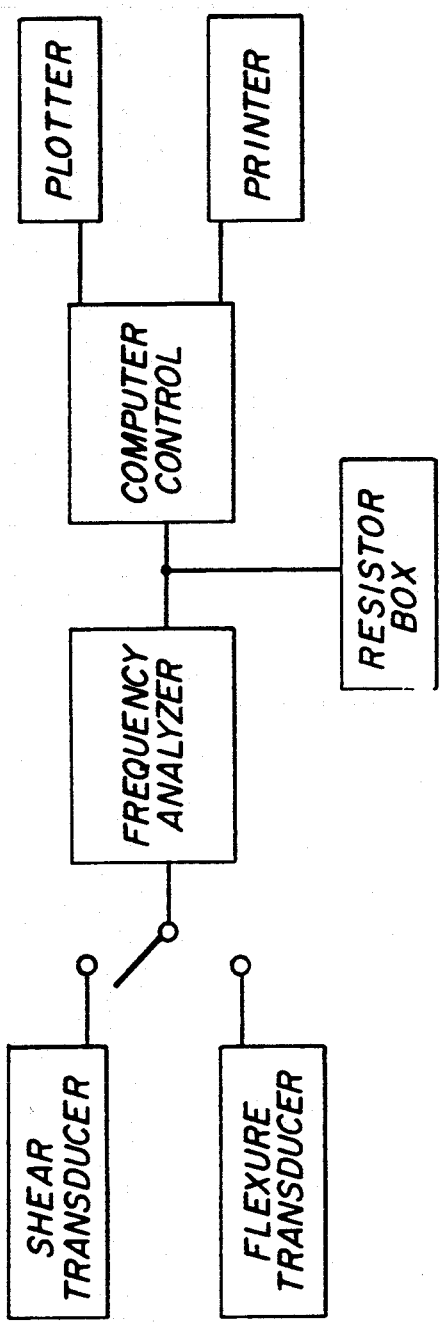
FIG. 7 is a function diagram for an automated measurement system with computer control, printer, and X—Y plotter.

Further, with inductive and capacitive coupling between the vibration force coil or coils and the velocity sensing coil or coils eliminated, the automated measurement system illustrated in FIG. 7 allows measurement at each frequency within 1 to 20 seconds instead of within 10 to 20 minutes as in prior dynamic mechanical measurement methods and apparatuses. In this figure a functional diagram of one such automated system is displayed where a commercially available two-channel frequency analyzer, personal computer, X-Y plotter and printer are combined through the switch, S, with the shear transducer shown in FIGS. 3, 3A or a corresponding flexure transducer (shown schematically in FIG. 5), and a standard 100-ohm resistor in the resistor box. The frequency analyzer provides the energizing alternating voltage $E = E_0 \sin \omega t$ across the driving force coil 1 (15 in FIG. 2) and the standard, known resistance, R as shown in FIG. 10, producing an alternating current, $I_1$, in coil 1. The frequency analyzer is capable only of determining the magnitude ratios and phase differences (i.e. complex or vector ratios) of two voltages, whereas the method hereinbefore described requires the complex or vector ratio of a current to a voltage. Therefore the voltage, $E_1 = I_1 R$ shown in FIG. 10 is put into one input channel of the analyzer, and the motional voltage, $E_2$, shown in FIG. 10 generated by coil 2 (13, 14 of FIG. 2, connected in series) is put into the other channel, and the complex (or vector) ratio $E_1/E_2$ is determined. Then, $$\vec{E_1}/\vec{E_2} = \vec{I_1}R/\vec{E_2}, \text{ and } \vec{I_1}/\vec{E_2} = \vec{E_1}/R\vec{E_2} \tag{16}$$

from which the necessary mechanical impedance is found as noted in Equation 8.

The magnitude, wave form, frequency, and frequency measurement intervals of the alternating voltage to be put across the force coil of the transducer are selected via the personal computer that runs the MS- DOS operating system. The frequency analyzer and plotter are controlled via a GPIB (IEEE-488) controller board. Numerical data summaries and data evaluations can be displayed on the computer monitor or printed; in every case the operator controls the data taking and display via the computer keyboard.

Obviously many modifications and variations of the present invention are possible in light of the above teachings.

What is claimed as new and desired to be secured by letters patent is:

1. An apparatus for determining the dynamic mechanical properties of materials comprising, in combination, means for creating a unidirectional magnetic flux field, means disposed within the flux field and movable in a plane transverse to the flux field, said last named means including at least a first coil disposed coplanar with the plane transverse to the flux field, a second coil rigidly coupled mechanically to the first coil and disposed coplanar with the plane transverse to the flux field, means for passing current through the first coil to move the first and second coils in a plane transverse to the electrical field and means connected to the second coil for measuring the electrical voltage generated in the second coil when the coils are vibrated within the magnetic flux field.

2. An apparatus according to claim 1 and further including means for determining the complex vector ratio of the current through the first coil to the motionally generated voltage in the second coil.

3. An apparatus according to claim 2 and further including means for holding a material sample, said last named means being mechanically connected to and movable with said first and second coils such that the material sample is deformed when said coils vibrate.

4. An apparatus for determining dynamic mechanical properties of materials comprising, in combination, a plurality of permanent magnets mounted in a frame to provide an air gap between opposite poles of the magnets, plate means suspended within the air gap and movable in a plane transverse to the magnetic flux within the air gap, a plurality of flat driving coils disposed on said plate means, means for causing alternating currents at frequencies from 0.1 to 100,000 cycles per second to pass through the driving coils whereby the plate means vibrates in a coplanar direction transverse to the magnetic flux, sensor coil means mounted on said plate means, means for measuring the alternating electrical voltage generated in said sensor coil means when said plate means is vibrated within the magnetic flux field and support means for retaining a material sample mechanically interconnected between the frame and said plate means whereby the material sample is stressed when the plate means is vibrated.

5. An apparatus according to claim 4 and further including means for determining the complex vector ratio of the alternating electrical current through the driving coils to the motionally generated alternating electrical voltage in the sensor coil.

6. An apparatus according to claim 4 wherein some of said plurality of driving coils are wound on said plate means in opposite directions so that the net inductive coupling between the driving and sensing coils is zero.

7. An apparatus according to claim 4 wherein said sensor coil means include two sensing coils having reverse winding directions and so disposed within the magnetic flux field to have the motional alternating voltages add and the inductive coupling voltages of the two sensing coils cancel.

8. An apparatus according to claim 4 and further including vibration isolation means for retaining said magnets for preventing the forces produced by the alternating electrical currents in the driving coils from being transmitted to the magnets of the sensing coils.

9. An apparatus according to claim 4 wherein said means for causing alternating currents to pass through the driving coils include computer control means for providing automated alternating electrical currents of preselected magnitudes and frequencies to be passed through said driving coils.

10. An apparatus according to claim 4 and further including computer control means for providing automated determinations of the complex ratio of electrical current in a driving coil or coils to the motional electromotive forces in velocity sensing coil or coils.

11. An apparatus according to claim 4 and further including computer control means for calculating and displaying dynamic mechanical properties of sample materials at various vibration frequencies.

12. An electrical circuit for determining the complex (vector) ratio of alternating electrical current, $I_1$, in a first, driving planar, coil or coils to the motional, alternating electrical voltage, $E_2$, generated in a coplanar, second and separate sensing planar coil or coils rigidly connected mechanically to the first, comprising, in combination, the coils aforesaid, a known, standard resistor, R, in electrical series with the first coil or coils, and a means for determining the complex (vector) voltage ratio of $E_1 = I_1 R$ across the resistor to the motionally generated voltage $E_2$, whereby the said $I_1/E_2$ ratio for the rigidly connected coils can be found from the relation $I_1/E_2 = E_1/E_2 R$.

13. An electrical circuit according to claim 12 wherein some of said coils are wound in opposite directions so that the net inductive coupling between the driving and sensing coils is zero.

14. An electrical circuit according to claim 12 wherein said sensor coil means comprises two sensing coils having opposite winding directions and so disposed within transverse magnetic flux fields to have their motional alternating electrical voltages add, and their inductive coupling voltages cancel.

15. An electrical circuit according to claim 12 and further including computer control means for providing automated determinations of the complex electrical voltage ratios, $E_1/E_2$, from which the complex vector electrical current ratio to electrical voltage ratio, $I_1/E_2$ is determined.

16. Apparatus for producing mechanical vibrations and sensing the extent or velocity of vibrational motion comprising, in combination, unidirectional magnetic flux means, at least two flat, planar coils lying in the same plane and arranged for movement transverse to the magnetic flux whereby the coils oscillate or vibrate in their common planar direction transverse to the magnetic flux when an alternating electrical current passes through at least one of said coils and a motional electrical voltage is produced in another of said coils when they are vibrated.

17. The apparatus according to claim 16 and further including means for passing known values of alternating electrical current through at least one of the coils whereby the force produced by the coils from the interaction of the magnetic flux and the electrical current can be calculated.

18. The apparatus according to claim 16 and further including means for measuring the motional electrical voltage generated in at least one of the coils when they are vibrated transversely to the magnetic flux directions whereby the velocity of the moving coils can be calculated.

19. The apparatus according to claim 16, and further including means for rigidly mounting said coils on a rigid plate, means for mounting a material to be tested adjacent to said plate whereby the test material is vibrationally deformed when alternating electrical currents are passed through at least one of the coils.

20. The apparatus according to claim 16, and further including means for eliminating the inductive coupling electrical voltage between said at least two coils from the force-producing current in one, while retaining the motional voltage produced in a second coil by their common velocity, comprising, in combination, the separation of a coil into two parts of identical shape and dimensions, and with equal numbers of turns, wound and connected so as to have opposite winding directions, means providing a corresponding reversal of magnetic flux directions transverse to each of the coil parts so that the motional voltages of each part add together when they are connected in electrical series, while the inductive voltages cancel to zero when the separated coil parts are located symmetrically to the first, currentcarrying, force coil, and means for interchanging the functions of producing vibrational force and sensing vibrational velocity between the first, unseparated coil and the second, separated coil.

* * * * *